(12) United States Patent
Yanuma et al.

(10) Patent No.: US 7,331,975 B2
(45) Date of Patent: Feb. 19, 2008

(54) BASKET FORCEPS

(75) Inventors: Yutaka Yanuma, Kunitachi (JP); Takaaki Komiya, Hachioji (JP)

(73) Assignee: Olympus Corporation, Tokyo (JP)

( * ) Notice: Subject to any disclaimer, the term of this patent is extended or adjusted under 35 U.S.C. 154(b) by 692 days.

(21) Appl. No.: 10/766,580

(22) Filed: Jan. 27, 2004

(65) Prior Publication Data
US 2004/0236351 A1 Nov. 25, 2004

(30) Foreign Application Priority Data
Jan. 31, 2003 (JP) .............................. 2003-024101
Jan. 19, 2004 (JP) .............................. 2004-010765

(51) Int. Cl.
*A61M 29/00* (2006.01)
(52) U.S. Cl. ....................... 606/200; 606/194; 606/198
(58) Field of Classification Search ................ 606/108, 606/159, 191, 192, 194, 198, 200; 604/27, 604/106, 107, 108, 109
See application file for complete search history.

(56) References Cited

U.S. PATENT DOCUMENTS 4,046,149 A    9/1977  Komiya
6,146,396 A *  11/2000 Konya et al. ................ 606/159

FOREIGN PATENT DOCUMENTS

| DE | 90 14 246    | 1/1991  |
| EP | 0 611 582 A2 | 8/1994  |
| EP | 0 875 263 A2 | 11/1998 |
| JP | 2-111353     | 4/1990  |

* cited by examiner

*Primary Examiner*—Michael J. Hayes
*Assistant Examiner*—Michael Mendoza
(74) *Attorney, Agent, or Firm*—Scully, Scott, Murphy & Presser, P.C.

(57) ABSTRACT

When a guide wire is inserted into a guide wire insertion hole formed in a tip member made of a resin tube, firstly, it is inserted into the guide wire insertion hole substantially from the center of the front surface of the resin tube. Then, the guide wire is guided to the outside of the resin tube through an opening formed in the outer periphery of the tube, and guided along the outer periphery of a basket unit.

11 Claims, 6 Drawing Sheets

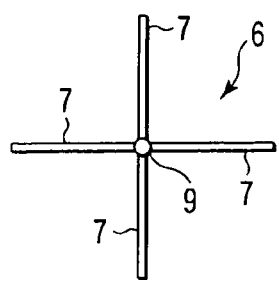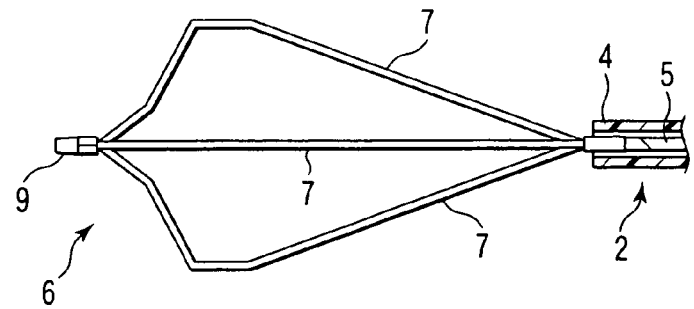
FIG. 2A  FIG. 2B
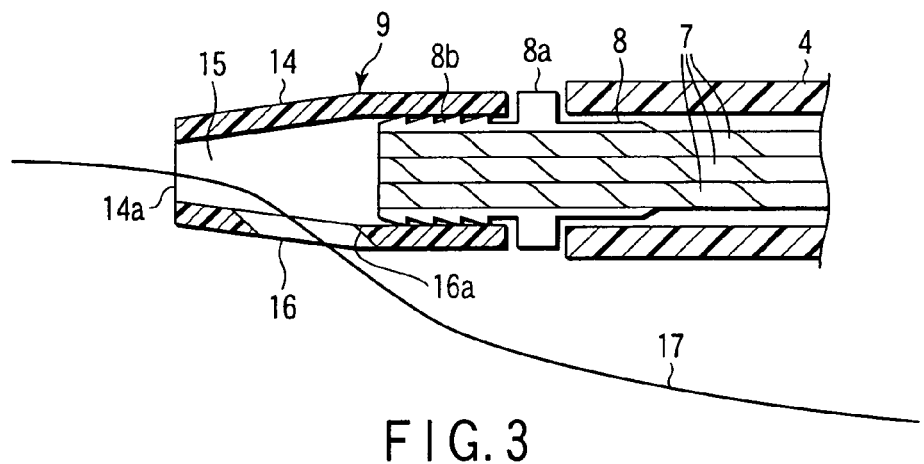
FIG. 3
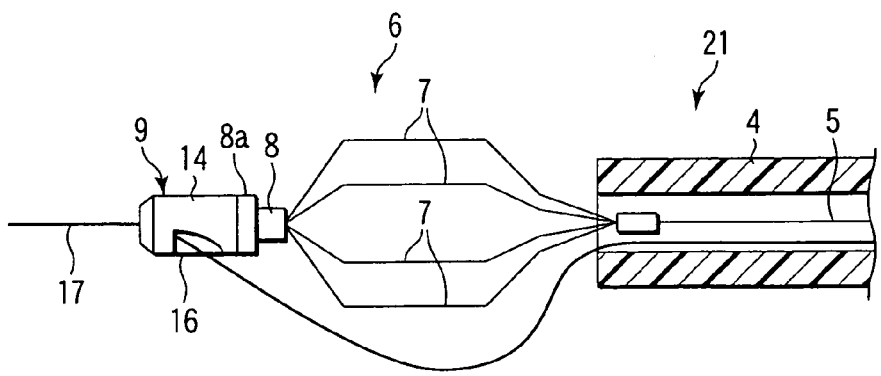
FIG. 4

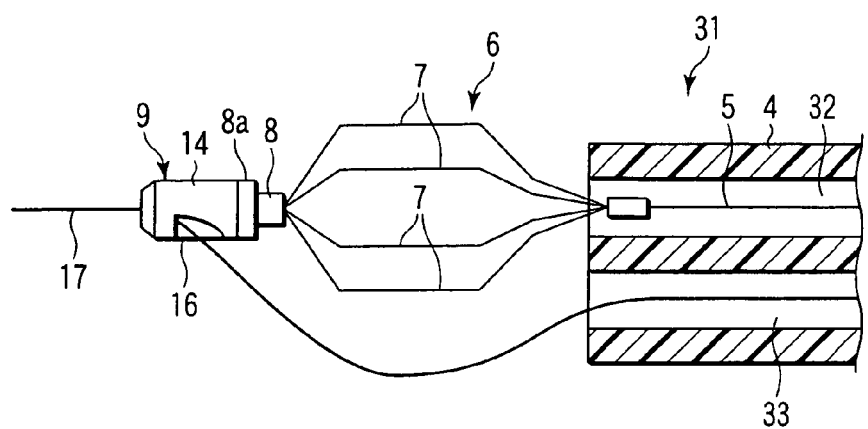
F I G. 5
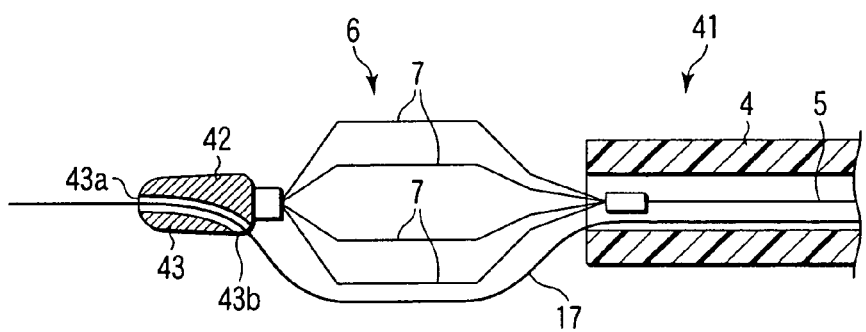
F I G. 6
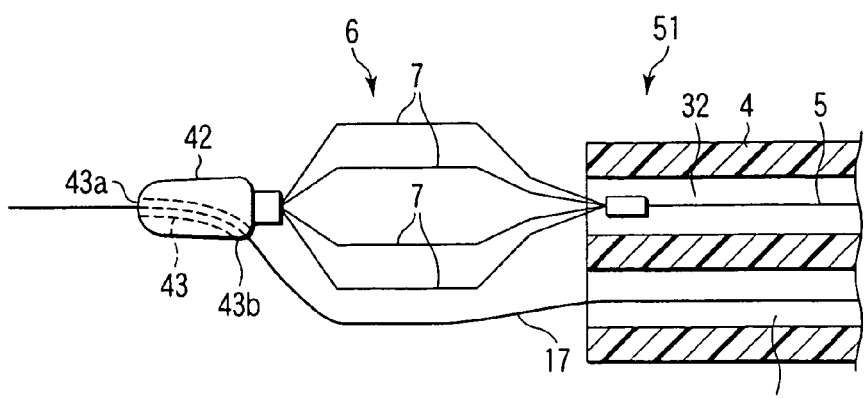
F I G. 7

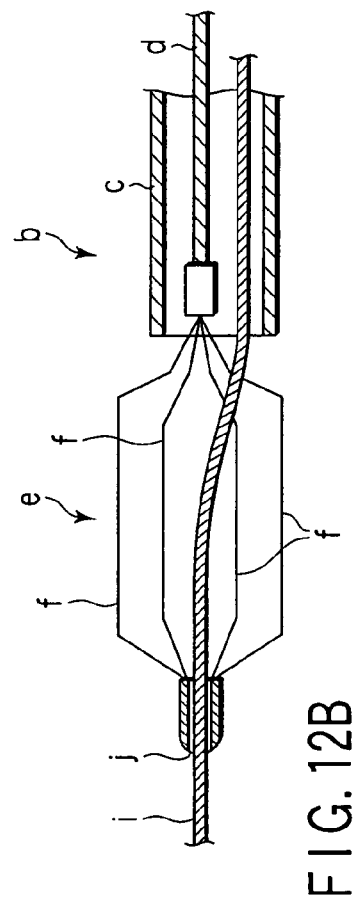
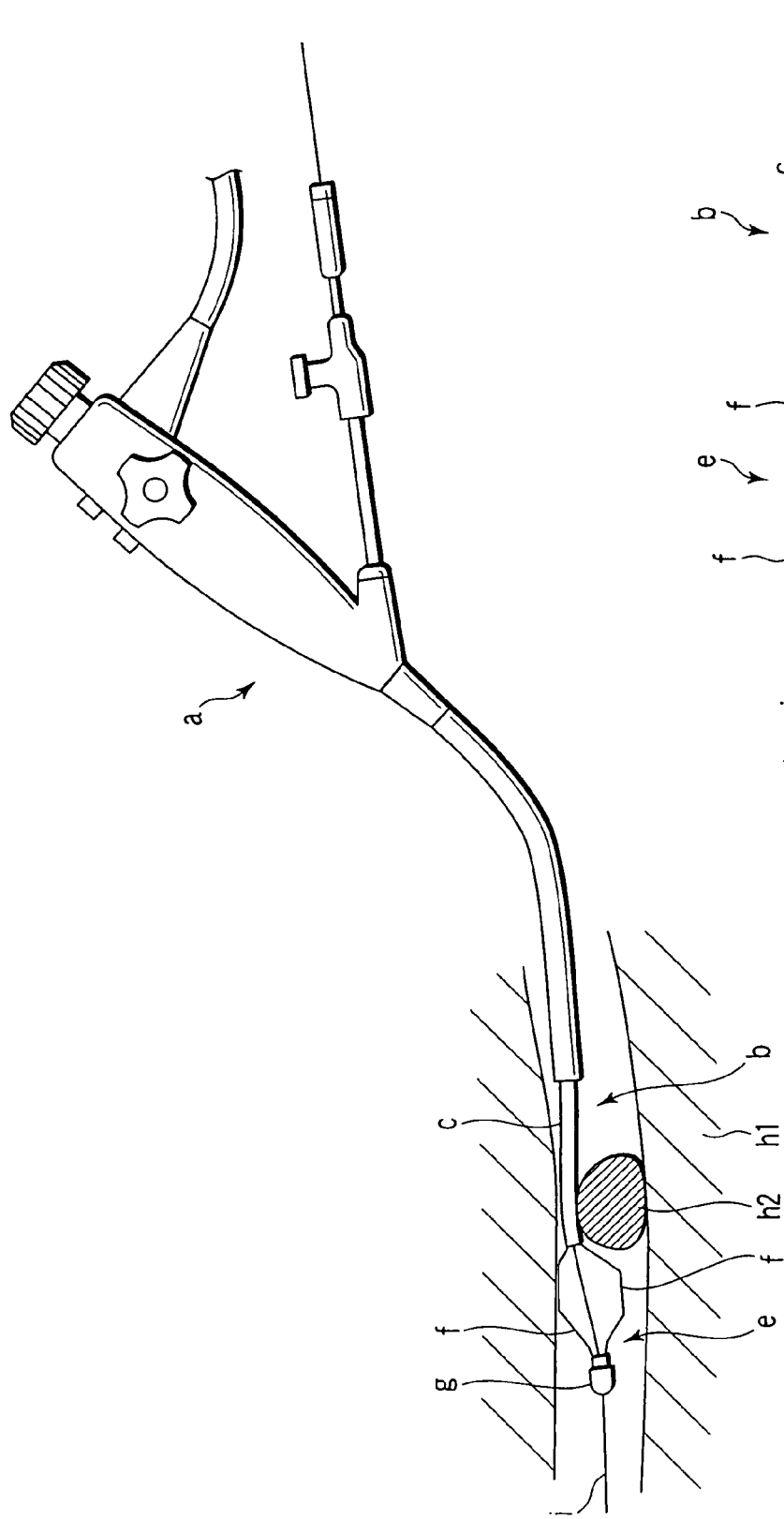
FIG. 12B
FIG. 12A

BASKET FORCEPS

CROSS-REFERENCE TO RELATED APPLICATIONS

This application is based upon and claims the benefit of priority from the prior Japanese Patent Applications No. 2003-024101, filed Jan. 31, 2003; and No. 2004-010765, Jan. 19, 2004, the entire contents of both of which are incorporated herein by reference.

BACKGROUND OF THE INVENTION

1. Field of the Invention

The present invention relates to basket forceps to be inserted into the body cavity of a patient to collect or shatter an alien substance therein, such as a calculus.

2. Description of the Related Art

Jpn. Pat. Appln. KOKAI Publication No. 2-111353, for example, discloses basket forceps for endoscopes used as a treatment instrument for removing, for example, gallstones. FIG. 12A schematically shows conventional basket forceps b used together with an endoscope a. The basket forceps b comprise a slim sheath c and handling wire d as shown in FIG. 12B. The handling wire d is movably inserted in the sheath c. A basket unit e is coupled to the distal end of the handling wire d. The basket unit e has a plurality of basket forming wires f. The proximal ends of the basket forming wires f are bundled and coupled to the tip of the handling wire d. The distal ends of the basket forming wires f are also bundled and secured to a tip member g. The respective portions of each basket forming wire f that are located close to the opposite ends of each wire f are expanded, thereby forming the basket unit e.

When the handling wire d is pushed and pulled relative to the sheath c, the basket unit e axially moves back and forth between a receipt position in which it is received in the sheath c, and an expanded position in which it is expanded in front of the sheath c.

In use, the basket forceps b are inserted into a body cavity of a patient, for example, into the bile duct with the basket unit e closed. After inserting the tip of the sheath c between the inner wall h1 of the bile duct and a gallstone h2, the basket unit e is opened to capture the gallstone h2 into the basket.

Further, in the basket forceps b, a wire insertion hole j for inserting therethrough a guide wire i is formed in the tip member g along its axis, as shown in FIG. 12B. The guide wire i is inserted through the wire insertion hole j of the tip member g and through the sheath c. Using the guide wire i inserted into the body before the basket forceps b, the forceps b are guided into the body.

BRIEF SUMMARY OF THE INVENTION

The present invention provides basket forceps that comprises: a slim sheath having a distal end and a proximal end; a handling wire having a distal end and a proximal end, and movably inserted in the sheath; a basket unit coupled to the distal end of the handling wire, the basket unit having a plurality of basket wires, each of the basket wires having front and rear ends, the front ends of the basket wires being bundled, the rear ends of the basket wires being also bundled, the basket wires thus providing a basket; a tip member secured to the bundled front end of the basket unit; a tubular basket-handling main unit coupled to the proximal end of the sheath and extending along an axis of the sheath; a basket handling unit coupled to the proximal end of the handling wire, the basket handling unit being slidable relative to the basket-handling main unit in a direction in which the handling wire is movable, the basket handling unit pushing and pulling the handling wire to move the basket unit between a receipt position in which the basket unit is received in the sheath, and an expanded position in which the basket unit is pushed out of the sheath and expanded in front of the sheath, the basket unit assuming the receipt position when the handling wire is pulled, and assuming the expanded position when the handling wire is pushed; and a guide wire insertion hole formed through the tip member and extending from a front surface of the tip member to an outer periphery of the tip member, a guide wire being inserted through the guide wire insertion hole.

Preferably, the sheath has an insertion lumen formed therein for inserting the handling wire and the guide wire.

Preferably, the sheath has an insertion lumen formed therein for inserting the handling wire, and a guide wire insertion lumen formed therein for inserting the guide wire.

Preferably, the tip member is formed of a resin tube, and a side opening is formed in an outer periphery of the resin tube, the side opening communicating with the guide wire insertion hole.

Preferably, the tip member is formed of a metal block, and the guide wire insertion hole is formed in the metal block.

Preferably, the tip member is provided with a wire bundling portion which bundles the basket wires, the tip member being also provided with the guide wire insertion hole that is not aligned with the wire bundling portion.

Preferably, the wire bundling portion has a metal tubular member, and the guide wire insertion hole has a resin block fitted on the tubular member.

Preferably, the block has a hole in which the tubular member is fitted, the guide wire insertion hole being formed in the block such that the guide wire insertion hole does not communicate with the hole.

Advantages of the invention will be set forth in the description which follows, and in part will be obvious from the description, or may be leaned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate an embodiment of the invention, and together with the general description given above and the detailed description of the embodiment given below, serve to explain the principles of the invention.

FIG. 2A is a front view illustrating a state in which the basket unit of the basket forceps of the first embodiment is expanded;

FIG. 2B is a side view illustrating the basket unit;

FIG. 3 is a longitudinal sectional view of an essential part of the first embodiment, illustrating a state in which a guide wire is inserted in a tip member provided at the tip of the basket forceps;

FIG. 4 is a longitudinal sectional view illustrating an essential part, i.e., the tip portion, of basket forceps according to a second embodiment;

FIG. 5 is a longitudinal sectional view illustrating an essential part, i.e., the tip portion, of basket forceps according to a third embodiment;

FIG. 6 is a longitudinal sectional view illustrating an essential part, i.e., the tip portion, of basket forceps according to a fourth embodiment;

FIG. 7 is a longitudinal sectional view illustrating an essential part, i.e., the tip portion, of basket forceps according to a fifth embodiment;

FIG. 12A is a schematic view illustrating a state of use of conventional basket forces; and FIG. 12B is a longitudinal sectional view illustrating a state in which the basket unit of the conventional basket forceps is expanded.

DETAILED DESCRIPTION OF THE INVENTION

Figure 1A:
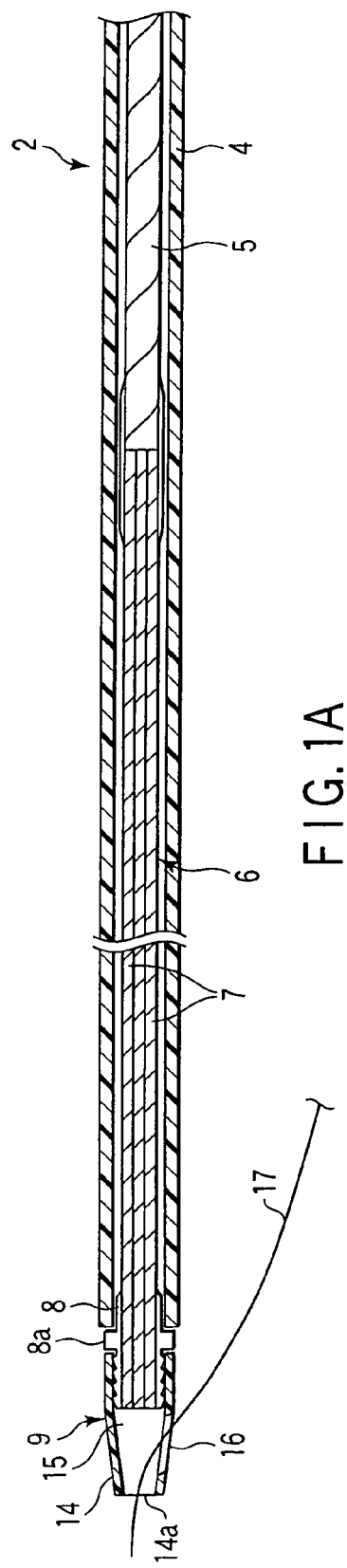
FIG. 1A is a longitudinal sectional view illustrating the tip portion of basket forceps, according to a first embodiment of the invention, viewed when the basket unit of the forceps is received in a sheath.

Referring first to FIGS. 1A to 3, a first embodiment of the invention will be described. FIGS. 1A and 1B show basket forceps 1 according to the first embodiment. FIG. 1A shows the tip portion of the forceps 1, while FIG. 1B shows the proximal portion of the basket forceps 1.

Figure 1B:
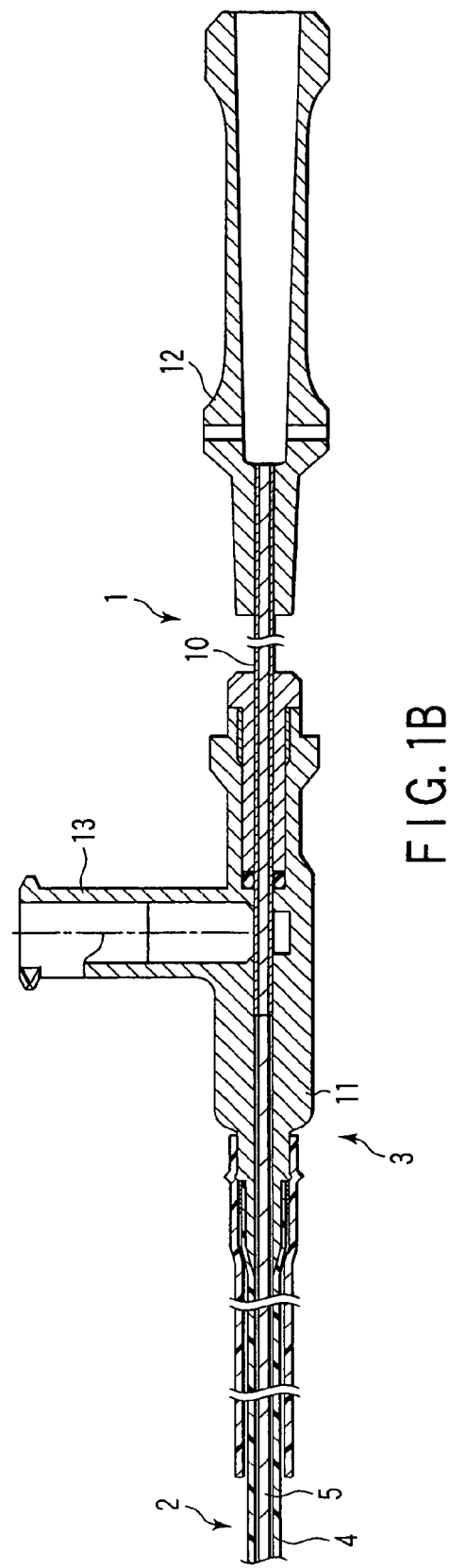
FIG. 1B is a longitudinal sectional view illustrating the handling unit of the basket forceps of the first embodiment.

As seen from FIGS. 1A and 1B, the basket forceps 1 of the first embodiment comprise a slim insertion unit 2 and a handling unit 3 positioned near the hands of an operator. The handling unit 3 is coupled to the proximal end of the insertion unit 2. The insertion unit 2 has a slim sheath 4 and handling wire 5. The handling wire 5 is axially movably inserted in the sheath 4. A basket unit 6 is coupled to the tip of the handling wire 5.

The basket unit 6 has a plurality of elastic wires 7 (four wires, in this embodiment, as shown in FIG. 2A) for forming a basket. The elastic wires 7 are bundled and coupled to the tip of the handling wire 5.

As shown in FIG. 1A, the tips of the elastic wires 7 are bundled and fixedly inserted in a metal coupling tube 8. The coupling tube 8 has a flange-shaped projection 8a projecting substantially from the center of the outer periphery of the tube 8. Further, the proximal end of a tubular tip member 9 is secured to the outer periphery of the distal end of the tube 8.

As shown in FIGS. 2A and 2B, the middle portion of each elastic wire 7 is warped toward the outside in a natural state. Thus, in the natural state, the elastic wires 7 cooperate to provide the basket unit 6 between the tip member 9 and handling wire 5.

As shown in FIG. 1B, the handling unit 3 has a longitudinal handling main unit 11. A wire hole 10 is formed in the main unit 11 along its axis. The handling wire 5 is inserted through the hole 10.

The proximal end of the sheath 4 is secured to the distal end of the handling main unit 11. The proximal end of the handling wire 5 is extended backward through the wire hole 10, and secured to a grip unit 12 by thermal press fitting. A cock 13 projects from the outer periphery of the handling main unit 11. A tube (not shown) is coupled to the cock 13 to enable, for example, a suction operation.

When using the basket forceps 1, the grip unit 12 is axially pushed and pulled relative to the handling main unit 11. As a result, the handling wire 5 is pushed and pulled relative to the sheath 4. Accordingly, the basket unit 6 is pushed and pulled axially. When the handling wire 5 is pulled, the basket unit 6 is received into the sheath 4 as shown in FIG. 1A. On the other hand, when the handling wire 5 is pushed, the basket unit 6 is pushed out of the sheath 4 as shown in FIG. 2B. When the basket unit 6 is completely out of the sheath 4, it is deformed toward outside to its expanded position because of the urging force of the elastic wires 7.

As shown in FIG. 3, the tip member 9 in this embodiment is formed of a resin tube 14. The proximal end of the resin tube 14 is fitted on the outer periphery of the distal end of the coupling tube 8. A saw-tooth pullout prevention portion 8b is provided on the outer periphery of the distal end of the coupling tube 8.

The internal space of the resin tube 14 provides a guide wire insertion hole 15. A side opening 16 that communicates with the guide wire insertion hole 15 is formed in the outer periphery of the distal end of the coupling tube 8. A guide wire 17 is inserted through the guide wire insertion hole 15 via the front opening 14a of the resin tube 14, and led to the outside via the side opening 16. Thus, the guide wire 17 is extended along the outer periphery of the basket unit 6 then along the sheath 4, and through the channel of an endoscope a (see FIG. 12A). As a result, the guide wire 17 reaches the handling unit 3. Further, the side opening 16 has a tapered surface 16a extending in the direction of extension of the guide wire 17.

The operation of the above structure will now be described. When using the endoscope basket forceps 1 according to the embodiment, the grip unit 12 is pulled backwardly relative to the handling main unit 11. As a result, the basket unit 6 is received in the sheath 4 as shown in FIG. 1A. With the basket unit thus closed, the insertion unit 2 of the basket forceps 1 are inserted into a body cavity of a patient, for example, the bile duct, through the channel of the endoscope a.

When the basket forceps 1 are inserted, they are guided into a body cavity along the guide wire 17 inserted therein before the forceps 1. Specifically, firstly, the guide wire 17 is inserted into the guide wire insertion hole 15 from the front opening 14a of the resin tube 14 of the tip member 9. Subsequently, the guide wire 17 is guided to the outside of the tube 14 through the side opening 16. Thus, the guide wire 17 is extended along the outer periphery of the basket unit 6.

The guide wire 17 is further extended along the outside of the sheath 4, and extended through the channel of the endoscope a (see FIG. 12A) toward the handling unit 3.

Thereafter, the guide wire 17 is inserted into a body cavity, and then the basket forceps 1 are inserted into the body cavity along the already inserted guide wire 17. The forceps 1 are pushed forward and guided along the guide wire 17 to a target portion, such as the interior of the bile duct, in the body cavity.

In this state, the grip unit 12 is pushed relative to the handling main unit 11, thereby forwarding the handling wire 5. As a result, the basket unit 6 is forwardly protruded from the tip of the sheath 4. At this time, the entire basket unit 6 is expanded outwardly because of the urging force of the elastic wires 7. When the basket unit 6 is completely pushed out of the sheath 4, the whole unit is elastically deformed in the form of a basket (expanded position) as shown in FIG. 2B. Alien substances, such as gallstones, in the body cavity can be captured into the basket unit 6 through between the expanded elastic wires 7. Thereafter, the basket forceps 1 are operated to collect or shatter the alien substances.

The above-described structure has the following advantages. In the endoscope basket forceps 1 of the first embodiment, the tip member 9 is formed of a resin tube 14 that has the side opening 16 formed in its outer periphery. The side opening 16 communicates with the guide wire insertion hole 15 of the resin tube 14. Accordingly, the guide wire 17 can be inserted into the guide wire insertion hole 15 through the front opening 14a of the resin tube 14 of the tip member 9, then led to the outside of the tube 14 through the side opening 16. Thus, the guide wire 17 is guided along the outer periphery of the basket unit 6, and prevented from passing through the interior of the basket unit 6. This facilitates the capture of, for example, gallstones into the basket unit 6.

Secondly, since the guide wire 17 is guided through the side opening 16 of the resin tube 14 to the outside, then guided along the outer periphery of the basket unit 6 to the outside of the sheath 4, it is not necessary to provide the interior of the sheath 4 with a space for passing the guide wire 17. As a result, the sheath 4 can be made thin and highly flexible.

Thirdly, since the guide wire 17 is inserted into the guide wire insertion hole 15 through the front opening 14a of the resin tube 14, the tip of the basket forceps 1 can be always aligned with the guide wire 17. This means that the tip of the basket forceps 1 can be easily guided to a target portion by the guide wire 17.

Fourthly, since the tapered surface 16a defining the side opening 16 extends in the direction of extension of the guide wire 17, the guide wire 17 can be easily inserted into the guide wire insertion hole 15 from the front opening 14a of the resin tube 14.

Although in the embodiment, a single side opening 16 is formed in the outer periphery of the resin tube 14, a plurality of side openings may be provided. Further, it is not always necessary to provide the side opening 16 with the tapered surface 16a that extends in the direction of extension of the guide wire 17.

FIG. 4 illustrates the tip portion of basket forceps 21 according to a second embodiment. The basket forceps 21 have almost the same structure as that of the first embodiment shown in FIGS. 1A to 3. Therefore, elements in FIG. 4 similar to those of the first embodiment are denoted by corresponding reference numerals and are not described. Only different elements will be described.

In the basket forceps 21 of the second embodiment, both the guide wire 17 and handling wire 5 are inserted in the sheath 4. More specifically, the guide wire 17 is extended along the outer periphery of the basket unit 6, and inserted in the insertion lumen in the sheath 4, in which the handling wire 5 is inserted. Therefore, when the basket forceps 21 of the second embodiment are inserted in the channel of the endoscope a (FIG. 12A), the guide wire 17 are prevented from being made naked in the channel. Accordingly, the guide wire 17 is prevented from being held by another element contained in the endoscope channel. This facilitates the insertion of the basket forceps 21, compared to the case where the guide wire 17 is made naked in the channel.

FIG. 5 shows the tip portion of basket forceps 31 according to a third embodiment of the invention. In the basket forceps 31 of this embodiment, the sheath 4 contains an insertion lumen 32 for the handling wire 5, and a guide wire insertion lumen 33. The guide wire 17 extended along the outer periphery of the basket unit 6 is inserted in the guide wire insertion lumen 33 that differs from the insertion lumen 32 for the handling wire 5.

In the third embodiment, when the basket forceps 31 are inserted in the channel of the endoscope a (FIG. 12A), the guide wire 17 is prevented from being made naked in the channel. Accordingly, the guide wire 17 is prevented from being held by another element contained in the endoscope channel, as in the third embodiment (FIG. 4). This facilitates the insertion of the basket forceps 31, compared to the case where the guide wire 17 is made naked in the channel.

FIG. 6 shows the tip portion of basket forceps 41 according to a fourth embodiment of the invention. The basket forceps 41 of this embodiment employ a tip member 42 formed of a metal block. A guide wire insertion hole 43 is formed in the metal block 42. The front opening 43a of the guide wire insertion hole 43 is formed in the front surface of the metal block 42. Further, the side opening 43b of the guide wire insertion hole 43 is formed in the outer periphery of the metal block 42.

In the basket forceps 41 of the fourth embodiment, the guide wire 17 is inserted into the guide wire insertion hole 43 from the front opening 43a, then guided to the outside of the block 42 through the side opening 43b. Accordingly, in the basket forceps 41 of the fourth embodiment, the guide wire 17 is extended along the outer periphery of the basket unit 6, without passing through the basket unit 6, as in the basket forceps 1 of the first embodiment (shown in FIGS. 1A to 3). As a result, gallstones, for example, can be easily captured by the basket unit 6.

Moreover, in the basket forceps 41 of the fourth embodiment, the guide wire 17 is inserted in the sheath 4 together with the handling wire 5, as in the basket forceps 21 of the second embodiment (shown in FIG. 4). Accordingly, when the basket forceps 41 of the fourth embodiment are inserted in the channel of the endoscope a (shown in FIG. 12A), the guide wire 17 is prevented from being made naked in the channel. This prevents the guide wire 17 from being held by another element contained in the endoscope channel, thereby facilitating the insertion of the basket forceps 41, compared to the case where the guide wire 17 is made naked in the channel.

FIG. 7 shows the tip portion of basket forceps 51 according to a fifth embodiment of the invention. In the basket forceps 51 of this embodiment, the sheath 4 contains an insertion lumen 32 for the handling wire 5, and a guide wire insertion lumen 33 for the guide wire 17, as in the basket forceps 31 of the third embodiment (shown in FIG. 5).

The basket forceps 51 of the fifth embodiment employ a tip member 42 formed of a metal block, as in the basket forceps 41 of the fourth embodiment (shown in FIG. 6). A guide wire insertion hole 43 is formed in the metal block 42. The front opening 43a of the guide wire insertion hole 43 is formed in the front surface of the metal block 42. Further, the side opening 43b of the guide wire insertion hole 43 is formed in the outer periphery of the metal block 42.

In the basket forceps 51 of the fifth embodiment, the guide wire 17 is inserted into the guide wire insertion hole 43 from the front opening 43a, then guided to the outside of the block 42 through the side opening 43b. Accordingly, in the basket forceps 51 of the fifth embodiment, the guide wire 17 is also extended along the outer periphery of the basket unit 6, without passing through the basket unit 6. As a result, gallstones, for example, can be easily captured by the basket unit 6.

Moreover, in the basket forceps 51 of the fifth embodiment, the guide wire 17 extended along the outer periphery of the basket unit 6 is inserted in the guide wire insertion lumen 33 in the sheath 4, which differs from the insertion lumen 32 for the handling wire 5. Accordingly, when the basket forceps 51 are inserted in the channel of the endoscope a (FIG. 12A), the guide wire 17 is prevented from being made naked in the channel. As a result, the guide wire 17 is prevented from being held by another element contained in the endoscope channel, as in the third embodiment (FIG. 4). This facilitates the insertion of the basket forceps 51, compared to the case where the guide wire 17 is made naked in the channel.

FIGS. 8A to 11 show a sixth embodiment of the invention. Basket forceps 61 according to the sixth embodiment is obtained by modifying the basket unit 6 of the basket forceps 1 of the first embodiment (see FIGS. 1A to 3) in the manner described below. The other structure is the same as that of the first embodiment. Therefore, elements in FIGS. 8A to 11 similar to those of the first embodiment are denoted by corresponding reference numerals and are not described. Only different elements will be described.

Figure 8A:
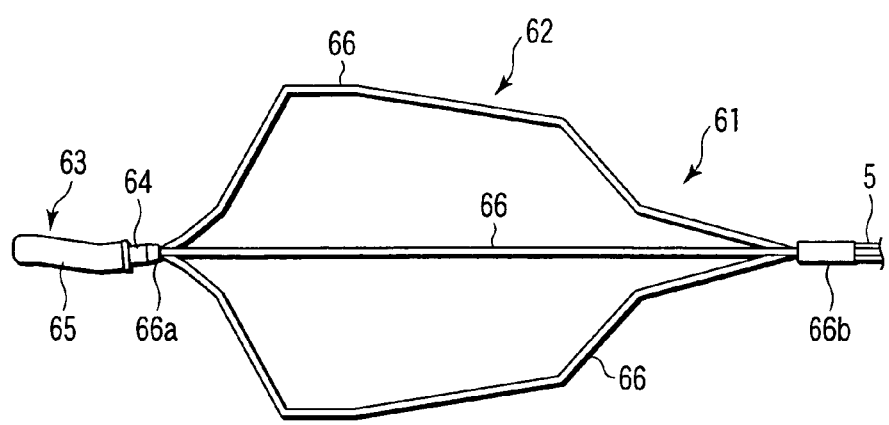
FIG. 8A is a side view illustrating a state in which the basket unit of basket forceps according to a sixth embodiment is expanded.
Figure 8B:
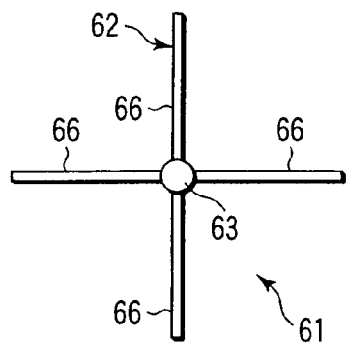
FIG. 8B is a front view illustrating a state in which the basket unit of the basket forceps according to the sixth embodiment is expanded.
Figure 9:
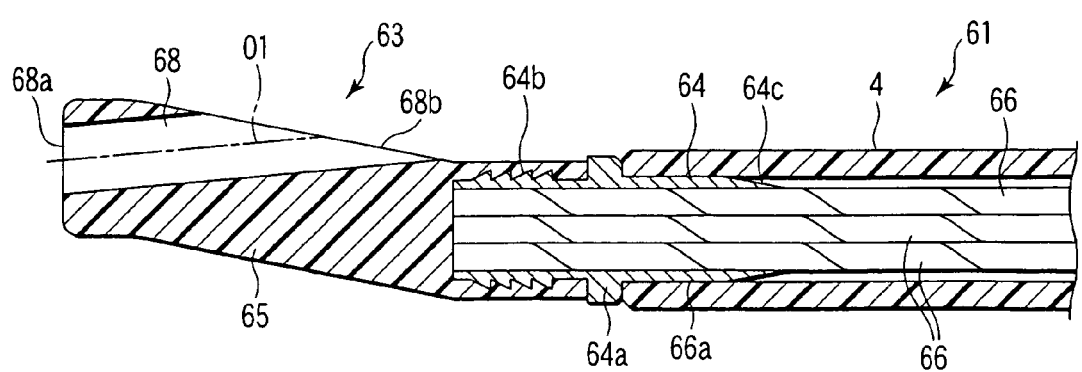
FIG. 9 is a longitudinal sectional view illustrating an essential part, i.e., the tip portion, of the basket forceps of the sixth embodiment.

FIGS. 8A and 8B illustrate the basket unit 62 of the basket forceps 61. As shown in FIG. 9, the tip member 63 of the basket unit 62 has a coupling tube 64 formed of a metal tubular member, and an elongated block 65 formed of a resin and fitted on the coupling tube 64.

As shown in FIG. 8B, the basket unit 62 has four elastic wires (basket wires) 66. The front ends of the elastic wires 66 are bundled into a wire bundling portion 66a, while the rear ends of the wires 66 are bundled into a wire bundling portion 66b. The rear wire bundling portion 66b is coupled to the tip of the handling wire 5.

Further, as shown in FIG. 9, the front wire bundling portion 66a is inserted in the metal coupling tube 64 and fixed therein.

The coupling tube 64 has a flange-shaped projection 64a projecting substantially from the center of the outer periphery of the tube. Further, a pullout prevention portion 64b having a saw-tooth-shaped section is provided on the outer periphery of the distal end of the coupling tube 64.

A tapered surface 64c having its outer diameter gradually reduced toward the proximal end of the coupling tube 64 is provided at the outer periphery of the proximal portion of the tube. When the handling wire 5 is pulled to pull the basket unit 62 into the sheath 4, the tapered surface 64c of the coupling tube 64 is inserted into the tip portion of the sheath 4.

Figure 10A:
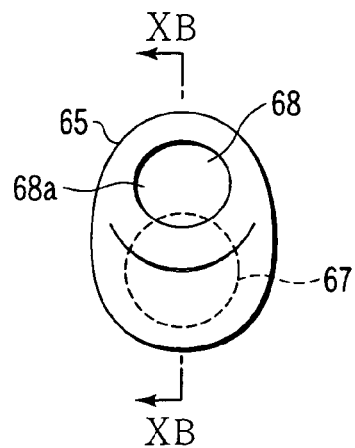
FIG. 10A is a front view illustrating a resin block incorporated in the basket forceps of the sixth embodiment.
Figure 10B:
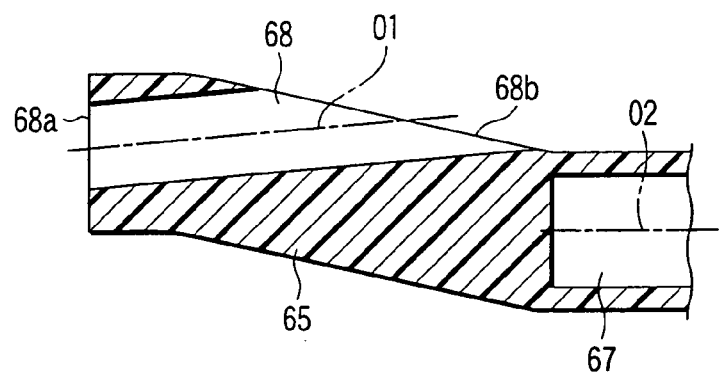
FIG. 10B is a sectional view taken along line XB-XB of FIG. 10A.
Figure 11:
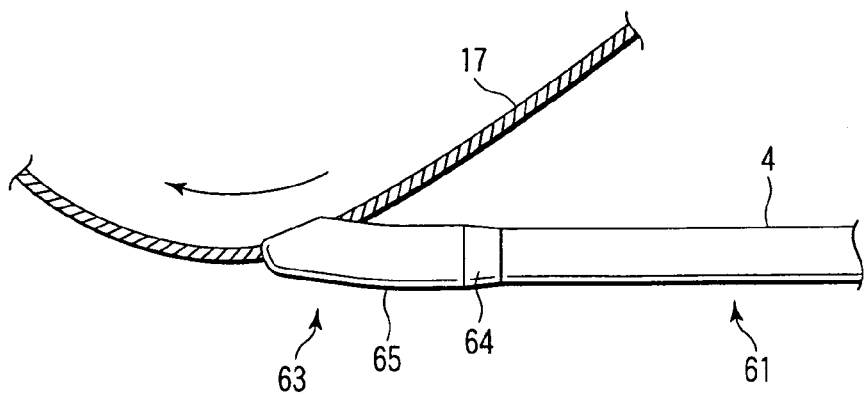
FIG. 11 is a side view useful in explaining the insertion of the basket forceps of the sixth embodiment along a guide wire.

Further, as shown in FIGS. 10A and 10B, the block 65 has a hole 67 formed in its proximal end, and a guide wire insertion hole 68 formed in its distal end. The axis O1 of the guide wire hole 68 is not aligned with the axis O2 of the hole 67 of the block 65. Thus, the hole 67 does not communicate with the guide wire insertion hole 68.

The distal end of the coupling tube 64 is press-fitted in the hole 67 of the block 65. In this state, the pullout prevention portion 64b of the coupling tube 64 digs into the peripheral surface of the hole 67 of the block 65. Further, an adhesive is provided on the peripheral surface of the hole 67 of the block 65 so that the coupling tube 64 is rigidly engaged with the inner periphery of the hole 67 and prevented from slipping out of the hole 67.

As shown in FIG. 10B, the guide wire insertion hole 68 extends from a front opening 68a formed in the front surface of the bock 65 of the tip member 63, to a peripheral opening 68b formed in the outer periphery of the block 65. The insertion hole 68 is positioned obliquely above and in front of the hole 67, i.e., these holes are eccentric to each other. In other words, the axis O1 of the guide wire insertion hole 68 is positioned obliquely with respect to the axis O2 of the hole 67.

The operation of the above structure will now be described. When using the basket forceps 61, the insertion unit 2 of the forceps is inserted into a body cavity, such as the bile duct, through the channel of the endoscope a (see FIG. 12A), with the basket unit 62 received in the sheath 4 as in the first embodiment.

The basket forceps 61 are inserted into the body cavity along the guide wire 17 beforehand inserted in the cavity. Before the guide wire 17 is inserted into the body cavity, it is inserted into the guide wire insertion hole 68 of the resin block 65 of the tip member 63 from the front opening 68a of the block, and guided to the outside of the block through the peripheral opening 68b of the block.

In this state, the guide wire 17 is inserted into the body cavity, and then the basket forceps 61 are inserted into the body cavity and guided to a target portion, such as the bile duct, along the already inserted guide wire 17.

After that, the basket unit 62 is forwardly pushed out of the sheath 4, as in the first embodiment. At this time, the basket unit 62 is outwardly expanded by the urging force of the elastic wires 66. When the basket unit 62 is completely pushed out of the sheath 4, the basket unit 62 is elastically deformed into a basket as shown in FIGS. 8A and 8B (expanded position). Alien substances, such as gallstones, in the body cavity can be captured into the basket unit 62 through between the expanded elastic wires 66. Thereafter, the basket forceps 61 are operated to collect or shatter the alien substances.

The above-described structure has the following advantage. In the tip member 63 of the basket unit 62 of the endoscope basket forceps 61 of the sixth embodiment, the coupling tube 64 in which the tips of the four elastic wires 66 are inserted is formed of a metal tubular member. Therefore, the wire bundling portion 66a that bundles the tips of the four elastic wires 66 is reinforced by the coupling tube 64.

Further, in the tip member 63, the wire bundling portion 66a that bundles the tips of the four elastic wires 66 is not aligned with the guide wire insertion hole 68. Therefore, the guide wire 17 inserted in the guide wire insertion hole 68 is kept out of contact with the wire bundling portion 66a, therefore prevented from being damaged by it.

Furthermore, since the guide wire 17 is inserted in the guide wire insertion hole 68 of the resin block 65, it is prevented from hitting against the edges of the guide wire insertion hole 68 and being damaged by them when the basket forceps 61 are inserted into a body cavity along the bent guide wire 17.

Furthermore, in the sixth embodiment, the coupling tube 64 that bundles the four elastic wires 66 is inserted in the hole 67 formed in the block 65 at a location different from that of the guide wire insertion hole 68. Therefore, the guide wire insertion hole 68 is prevented from being occupied by the adhesive coated on the inner surface of the hole 67. If, on the other hand, the hole 67 is aligned with the guide wire insertion hole 68, it is not necessary to take care, when coating the inner surface of the hole 67 with an adhesive, not to fill the guide wire insertion hole 68 with the adhesive. Thus, the basket unit 62 of the basket forceps can be produced easily.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. Basket forceps comprising:
   a slim sheath having a distal end and a proximal end;
   a handling wire having a distal end and a proximal end, and movably inserted in the sheath;
   a basket unit coupled to the distal end of the handling wire, the basket unit having a plurality of basket wires, each of the basket wires having front and rear ends, the front ends of the basket wires being bundled, the rear ends of the basket wires being also bundled, the basket wires thus providing a basket;
   a tip member secured to the bundled front end of the basket unit;
   a tubular basket-handling main unit coupled to the proximal end of the sheath and extending along an axis of the sheath;
   a basket handling unit coupled to the proximal end of the handling wire, the basket handling unit being slidable relative to the basket-handling main unit in a direction in which the handling wire is movable, the basket handling unit pushing and pulling the handling wire to move the basket unit between a receipt position in which the basket unit is received in the sheath, and an expanded position in which the basket unit is pushed out of the sheath and expanded in front of the sheath, the basket unit assuming the receipt position when the handling wire is pulled, and assuming the expanded position when the handling wire is pushed; and
   a guide wire insertion hole formed through the tip member and extending from a front opening provided on a front surface of the tip member to a side opening provided on an outer periphery of the tip member, wherein an axis of the side opening has an angle formed in a direction away from the axis of the basket.

2. The basket forceps according to claim 1, wherein the sheath has an insertion lumen formed therein for inserting the handling wire and the guide wire.

3. The basket forceps according to claim 1, wherein the sheath has an insertion lumen formed therein for inserting the handling wire, and a guide wire insertion lumen formed therein for inserting the guide wire.

4. The basket forceps according to claim 1, wherein the tip member is formed of a resin tube, and a side opening is formed in an outer periphery of the resin tube, the side opening communicating with the guide wire insertion hole.

5. The basket forceps according to claim 1, wherein the tip member is formed of a metal block, and the guide wire insertion hole is formed in the metal block.

6. The basket forceps according to claim 1, wherein the tip member is provided with a wire bundling portion which bundles the basket wires, the tip member being also provided with the guide wire insertion hole which is not aligned with the wire bundling portion.

7. The basket forceps according to claim 6, wherein the wire bundling portion has a metal tubular member, and the guide wire insertion hole has a resin block fitted on the tubular member.

8. The basket forceps according to claim 7, wherein the block has a hole in which the tubular member is fitted, the guide wire insertion hole being formed in the block such that the guide wire insertion hole does not communicate with the hole.

9. The basket forceps according to claim 6, wherein the side opening of the tip member is provided on the distal side rather than the wire bundling portion.

10. Basket forceps comprising;
    a slim sheath having a distal end and a proximal end;
    a handling wire having a distal end and a proximal end, and movably inserted in the sheath;
    a basket unit coupled to the distal end of the handling wire, the basket unit having a plurality of basket wires, each of the basket wires having front and rear ends, the front ends of the basket wires being bundled, the rear ends of the basket wires being also bundled, the basket wires thus providing a basket;
    a tip member secured to the bundled front end of the basket unit;
    a tubular basket-handling main unit coupled to the proximal end of the sheath and extending along an axis of the sheath;
    a basket handling unit coupled to the proximal end of the handling wire, the basket handling unit being slidable relative to the basket-handling main unit in a direction in which the handling wire is movable, the basket handling unit pushing and pulling the handling wire to move the basket unit between a receipt position in which the basket unit is received in the sheath, and an expanded position in which the basket unit is pushed out of the sheath and expanded in front of the sheath, the basket unit assuming the receipt position when the handling wire is pulled, and assuming the expanded position when the handling wire is pushed; and
    a guide wire insertion hole formed through the tip member and extending from a front opening provided on a front surface of the tip member to a rear end opening provided at a position different from that of the bundling portion of the front end of the basket unit in a rear end of the tip member, wherein the guide wire is lead in a direction away from the center of the basket.

11. Basket forceps comprising:
    a slim sheath having a distal end and a proximal end;
    a handling wire having a distal end and a proximal end, and movably inserted in the sheath;
    a basket unit coupled to the distal end of the handling wire, the basket unit having a plurality of basket wires, each of the basket wires having front and rear ends, the front ends of the basket wires being bundled, the rear ends of the basket wires being also bundled, the basket wires thus providing a basket;
    a tip member secured to the bundled front end of the basket unit;
    a tubular basket-handling main unit coupled to the proximal end of the sheath and extending along an axis of the sheath;
    a basket handling unit coupled to the proximal end of the handling wire, the basket handling unit being slidable relative to the basket-handling main unit in a direction in which the handling wire is movable, the basket handling unit pushing and pulling the handling wire to move the basket unit between a receipt position in which the basket unit is received in the sheath, and an expanded position in which the basket unit is pushed out of the sheath and expanded in front of the sheath, the basket unit assuming the receipt position when the handling wire is pulled, and assuming the expanded position when the handling wire is pushed: and a guide wire insertion hole formed through the tip member and extending from a front surface of the tip member to an outer periphery of the tip member, a guide wire being inserted through the guide wire insertion hole;

wherein the sheath has an insertion lumen formed therein for inserting the handling wire, and a guide wire insertion lumen formed therein for inserting the guide wire.

* * * * *